US00PP23778P3

(12) United States Plant Patent
Zaiger et al.

(10) Patent No.: US PP23,778 P3
(45) Date of Patent: Jul. 30, 2013

(54) INTERSPECIFIC TREE NAMED 'FESTIVAL RED'

(50) Latin Name: *Interspecific Prunus species*
Varietal Denomination: Festival Red

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 72 days.

(21) Appl. No.: 13/374,092

(22) Filed: Dec. 12, 2011

(65) Prior Publication Data

US 2013/0152250 P1 Jun. 13, 2013

(51) Int. Cl.
*A01H 5/00* (2006.01)

(52) U.S. Cl.
USPC ..... Plt./180

(58) Field of Classification Search
USPC ..... Plt./180
See application file for complete search history.

*Primary Examiner* — Annette Para

(57) ABSTRACT

A new and distinct variety of interspecific tree (*Prunus* species). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consists of the following combination of desirable features:

1. Vigorous, upright tree growth.
2. Heavy and regular bearer of large size fruit.
3. Fruit with very good flavor and eating quality.
4. Fruit with attractive dark red skin color.
5. Fruit with attractive red flesh.
6. Fruit with good handling and shipping quality.

1 Drawing Sheet

Botanical designation: Interspecific *Prunus* species.
Variety denomination: 'Festival Red'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of plum and interspecifics, which are known to us, and mentioned herein, the non-patented proprietary interspecific seedlings '288LF477' and '35GF34', 'Geo Pride' Interspecific (U.S. Plant Pat. No. 10,386) and 'Flavor Treat' Interspecific (U.S. Plant Pat. No. 12,936).

STATEMENT REGARDING FEDERALLY SPONSORED RESEARCH AND DEVELOPMENT

Not applicable.

ORIGIN OF THE VARIETY

The new and distinct interspecific tree was originated by us from crosses between the following species *Prunus salicina*, (*Prunus salicina*×*Prunus armeniaca*) and (*Prunus armeniaca*×*Prunus persica*). The present variety was selected as a first generation seedling from a cross between our proprietary interspecific seedling '288LF477' (non-patented) and 'Flavor Treat' Interspecific (U.S. Plant Pat. No. 12,936). The seed parent '288LF477' (non-patented) originated from crosses of 'Geo Pride' Interspecific (U.S. Plant Pat. No. 10,386) and the proprietary interspecific seedling selection '35GF34' (non-patented). We budded a large number of these seedlings to older 'Nemaguard' Rootstock (non-patented) trees to induce earlier fruit production for evaluation. Under close and careful observation the present seedling exhibited desirable fruit and tree characteristics and was selected in 2001 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of interspecific tree, which includes Plums, Plumcot and Peachcot in its parentage, is of large size, vigorous, upright growth and a regular and productive bearer of large size, clingstone fruit with very good flavor and eating quality. The fruit is further characterized by having an attractive dark red skin color, firm red flesh and being relatively uniform in size throughout the tree. In comparison to the proprietary seed parent '288LF477' (non-patented) the fruit of the new variety has firmer, darker red flesh and is approximately 11 days earlier in maturity. In comparison to its pollen parent 'Flavor Treat' Interspecific (U.S. Plant Pat. No. 12,936) the fruit of the new variety has red flesh instead of yellow and is approximately 73 days earlier in maturity. In comparison to the commercial variety 'Dapple Fire' Interspecific (U.S. Plant Pat. No. 12,409) the fruit of the new variety is firmer, has darker red skin and flesh color and is approximately 4 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 8 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 8 year old specimens grown near Modesto, Calif., with color in accordance with Munsell Book of Color.

Tree:

*Size*.—Large, pruned to 3 to 3.5 meters in height and width for economical harvesting of fruit. Varies with different cultural practices.

*Vigor*.—Vigorous, tree growth of approximately 1.5 to 2 meters the first growing season. Varies with cultural practices, soil type, fertility and climatic conditions.

*Form*.—Upright, usually pruned to vase shape to allow more sunlight to center of tree to enhance fruit color and health of fruit wood.

*Branching habit*.—Upright, crotch angle approximately 45°, increases with heavy crop load.

*Productivity*.—Productive, thinning and spacing of fruit necessary for desired market size. Fruit set varies with climatic conditions during bloom season.

*Bearer*.—Regular, adequate fruit set 6 consecutive years. No alternate bearing observed.

*Fertility*.—Self sterile, pollinator required.

*Density*.—Medium dense, controlled by pruning.

*Hardiness*.—Hardy in all stone fruit growing areas of California. Tree grown in USDA Hardiness Zone 9. Winter chilling requirement approximately 600 hours at or below 45° F.

Trunk:

*Size*.—Large. Average circumference 50.8 cm at 22.9 cm above ground on 8 year old tree.

*Stocky*.—Medium stocky.

*Texture*.—Medium shaggy, roughness increases with age of tree.

*Color*.—Varies from 2.5Y 4/2 to 5Y 6/2.

Branches:

*Size*.—Medium. Average circumference 9.1 cm at 1 meter above ground. Crotch angle approximately 45°, increases with heavy crop load.

*Surface texture*.—New growth relatively smooth. Mature growth medium rough, roughness increases with age.

*Lenticels*.—Size — medium. Average length 2.6 mm. Average width 1.2 mm. Average number 17 in a 25.8 sq cm section. Color varies from 5YR 5/10 to 5YR 4/8.

*Color*.—New growth varies from 5GY 5/6 to 5GY 4/6. Mature growth varies from 7.5YR 3/4 to 7.5YR 2/4, varies with age of growth.

Leaves:

*Size*.—Large. Average length 102.7 mm. Average width 50.2 mm.

*Form*.—Oblanceolate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins, glabrous. Lower surface relatively smooth, except for small ridges created by midrib and pinnate venation, glabrous.

*Petiole*.—Average length 16.4 mm. Average width 1.6 mm. Longitudinally grooved. Surface — glabrous. Color varies from 5GY 6/6 to 5R 3/6.

*Glands*.—Type — globose. Size — small to medium. Average length 0.8 mm. Average diameter 0.5 mm. Average number 3, varies from 2 to 5. Located primarily on upper portion of petiole, base of leaf blade. Color varies from 2.5GY 6/6 to 5GY 6/6.

*Stipules*.—Average number 2. Average length 11.3 mm. Margin — pectinate. Color varies from 5GY 5/6 to 5GY 4/6.

*Color*.—Upper surface varies from 5GY 3/6 to 7.5GY 3/4. Lower surface varies from 7.5GY 5/4 to 7.5GY 4/4. Midvein color 5GY 7/6.

Flower buds:

*Size*.—Small to medium. Average length 8.7 mm. Average diameter 5.6 mm.

*Hardiness*.—Hardy with respect to California winters.

*Form*.—Plump, conical, becoming elongated just before opening.

*Pedicel*.—Average length 12.7 mm. Average width 0.6 mm. Surface — glabrous. Color varies from 5GY 5/6 to 5GY 5/8.

*Color*.—N 9.5/ (white).

*Number of buds per spur*.—Average number 9, varies from 8 to 10. Varies with age of spur.

Flowers:

*Blooming period*.—Date of First Bloom Feb. 20, 2011. Date of Petal Fall Mar. 2, 2011, varies slightly with climatic conditions.

*Size*.—Small to medium. Average height 12.3 mm. Average diameter 20.1 mm.

*Petals*.—Normally 5, alternately arranged to sepals. Size — medium. Average length 9.5 mm. Average width 7.4 mm. Form — globose. Margin — sinuate. Both upper and lower surfaces glabrous. Color N 9.5/ (white).

*Sepals*.—Normally 5, alternately arranged to petals. Size — small. Shape — triangular, apex rounded. Margin — entire. Average length 3.4 mm. Average width 2.3 mm. Both upper and lower surfaces glabrous. Color — upper surface varies from 5GY 5/6 to 5GY 5/8. Lower surface varies from 5GY 6/4 to 5GY 5/6.

*Stamens*.—Average number per flower 19. Average filament length 6.5 mm. Filament color N 9.5/ (white). Anther color varies from 5Y 8.5/6 to 5Y 8/6.

*Pollen*.—Self sterile, pollinator required. Color varies from 5Y 7/6 to 5Y 7/8.

*Pistil*.—Normally 1. Surface — glabrous. Average length 8.9 mm. Position of stigma average of 2.1 mm below anthers. Color varies from 2.5GY 6/6 to 5GY 6/6.

*Fragrance*.—Slight aroma.

*Color*.—N 9.5/ (white).

*Number flowers per flower bud*.—Average 2, varies from 1 to 3.

*Pedicel*.—Average length 13.1 mm. Average width 0.6 mm. Surface — glabrous. Color varies from 5GY 5/6 to 5GY 5/8.

Fruit:

*Maturity when described*.—Firm ripe.

*Date of first picking*.—Jun. 27, 2011.

*Date of last picking*.—Jul. 7, 2011, varies slightly with climatic conditions.

*Size*.—Large. Average diameter axially 55.0 mm. Average transversely in suture plane 67.8 mm. Average weight 175.1 grams, average weight varies slightly with fertility of the soil, amount of thinning and climatic conditions.

*Form*.—Globose.

*Suture*.—Very slightly lipped, extends from base to apex.

*Ventral surface*.—Very slightly lipped.

*Apex*.—Slightly retuse.

*Base*.—Flat to very slightly retuse.

*Stem cavity*.—Rounded to slightly elongated in suture plane. Average depth 3.2 mm. Average diameter 3.4 mm.

Stem:

*Size*.—Medium. Average length 15.8 mm. Average diameter 2.0 mm.

*Color*.—Varies from 7.5GY 5/8 to 5YR 3/6.

Flesh:

*Ripens*.—Evenly.

*Texture*.—Firm, meaty.

*Fibers*.—Few, small, tender.

*Firmness*.—Good, comparable to commercial varieties of interspecifics.

*Aroma*.—Slight.

*Amydgalin*.—Undetected.

*Eating quality*.—Very good.

*Flavor*.—Very good, good balance between acid and sugar.

*Juice*.—Heavy, enhances flavor.

*Brix*.—Average Brix 15.1°, varies slightly with amount of fruit per tree and climatic conditions.

*Color*.—Varies from 10YR 9/4 to 5R 2/8.

*Pit cavity*.—Average length 24.2 mm. Average width 22.5 mm. Average depth 7.0 mm. Color varies from 7.5R 4/8 to 7.5R 3/8.

Skin:

*Thickness*.—Medium.

*Surface*.—Relatively smooth.

*Bloom*.—Moderate amount, complete amount.

*Tendency to crack*.—Very slight with heavy rain, varies with fruit maturity.

*Color*.—Ground color green-yellow, varies from 2.5GY 8/8 to 2.5GY 6/8. Overspread with 10Y 6/10 to 5R 3/10.

*Tenacity*.—Tenacious to flesh.

*Astringency*.—Undetected.

Stone:

*Type*.—Clingstone.

*Size*.—Medium to large. Average length 23.6 mm. Average width 21.7 mm. Average thickness 12.0 mm.

*Form*.—Obovoid.

*Base*.—Flat.

*Apex*.—Pointed. Average length 1.6 mm.

*Surface*.—Small pits throughout.

*Sides*.—Unequal, one side extending further outward from suture plane.

*Ridges*.—Small, narrow ridge on each side of suture extending from base to apex.

*Tendency to split*.—None.

*Color*.—Varies from 10YR 7/8 to 7.5YR 5/10 when dry.

Kernel:

*Size*.—Medium. Average length 12.2 mm. Average width 10.5 mm. Average depth 5.2 mm.

*Form*.—Ovoid.

*Viability*.—Viable, complete embryo development.

*Skin*.—Color varies from 2.5Y 8.5/6 to 5Y 9/6.

Use: Dessert.

*Market*.—Local and long distance.

Keeping quality: Good, held firm in cold storage 3 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

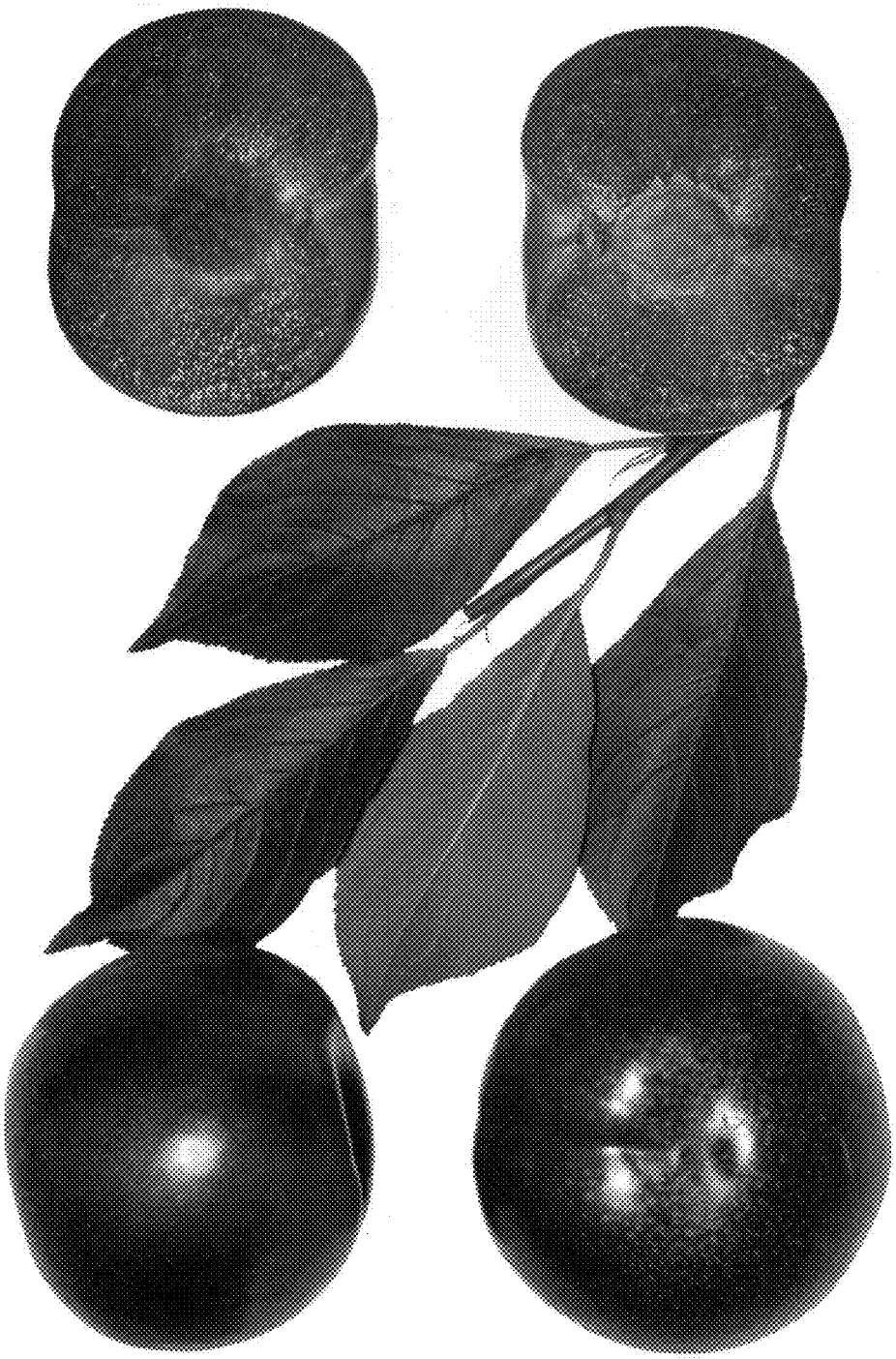

* * * * *